United States Patent [19]
Graiver et al.

[11] Patent Number: 5,880,304
[45] Date of Patent: Mar. 9, 1999

[54] METHOD OF MAKING ORGANOSILICON CARBONYL COMPOUNDS

[75] Inventors: Daniel Graiver, Midland, Mich.; Aaron Quoc Khieu, Coon Rapids, Minn.; Binh Thanh Nguyen, Midland, Mich.

[73] Assignee: Dow Corning Corporation, Midland, Mich.

[21] Appl. No.: 813,025

[22] Filed: Mar. 6, 1997

[51] Int. Cl.$^6$ ...................................................... C07F 7/04
[52] U.S. Cl. ........................ 556/442; 556/436; 556/450; 549/214; 528/12; 528/15; 528/32
[58] Field of Search .................................. 556/436, 442, 556/450; 528/32, 12, 15; 549/214

[56] References Cited

U.S. PATENT DOCUMENTS

| | | | |
|---|---|---|---|
| 2,588,083 | 3/1952 | Burkhard | 260/448 |
| 2,591,736 | 4/1952 | Sommer | 260/448 |
| 2,805,235 | 9/1957 | Kiffer | 556/436 |
| 3,145,232 | 8/1964 | Thompson | 260/586 |
| 3,202,704 | 8/1965 | Perry | 260/533 |
| 3,344,104 | 9/1967 | Hyde | 260/32.8 |
| 4,424,392 | 1/1984 | Petty | 556/436 |
| 4,609,574 | 9/1986 | Keryk | 427/407 |
| 4,658,044 | 4/1987 | Ravenscroft | 549/415 |

FOREIGN PATENT DOCUMENTS

| | | |
|---|---|---|
| 1132114 | 6/1962 | Germany . |
| 757355 | 9/1956 | United Kingdom . |

OTHER PUBLICATIONS

Movsumzade, E.M. Condensation of styrene and acrolein with methyldichlorosilane. Azerb. Neft. Khoz. (1972), 52(1), 39–40, 49.

Criegee, R. and Korber, H. Ozone Reactions with Organic Compounds, Advances in Chemistry Series 112, American Chemical Society, washington, D.C. 1972, pp. 22–34.

Russian Chemical Reviews, vol. 36, No. 4, pp. 284–294, Apr. 1967.
Journal American Chemistry Society, vol. 72, pp. 1935–1939, May 1950.
Z. Chem., 5, Jg, Heft 3, pp. 97–103, 1965.
Organic Chemistry, Prentice Hall, pp. 315–316, 1987.
Journal American Chemical Society, vol. 113, pp. 8168–8169, 1991.
Journal American Chemical Society, vol. 79, pp. 3073–3077, Jun. 1957.
Journal Organic Chemistry, vol. 35, No. 12, pp. 4180–4183, 1970.
Journal Organic Chemistry, vol. 23, pp. 627–628, Apr. 1958.
Journal Organic Chemistry, vol. 24, pp. 427–428, Mar. 1959.
F. Asinger, Ber., Jahrg. 75, 656–660, 1942.
Chemical Reviews, vol. 27, No. 3, pp. 437–493, Dec. 1940.
Chemical Reviews, vol. 58, No. 5, pp. 925–1010, Oct. 1958.
Journal of Organic Chemistry, vol. 35, No. 11, pp. 3879+, 1970.
Bulletin of the Academy of Sciences, USSR, Division of Chemical Science, No. 8, pp. 1405–1407, Aug. 1966.
Journal of General Chemistry of the USSR, vol. 38, No. 10, pp. 2234–2236, Oct. 1968.
Journal of General Chemistry of the USSR, vol. 38, No. 2, pp. 380–385, Feb. 1968.

*Primary Examiner*—Melvyn I. Marquis
*Assistant Examiner*—Mark W. Milstead
*Attorney, Agent, or Firm*—James De Cesare

[57] ABSTRACT

Organosilicon aldehydes and ketones are prepared by a method in which an organosilicon compound containing ozonide functionality is first formed by exposing an organosilicon compound containing unsaturation to ozone. The organosilicon compound containing ozonide functionality is then reduced to the corresponding organosilicon aldehyde or ketone with a reducing agent. One preferred reducing agent is a combination of zinc and acetic acid. Complete conversion of the ozonide to the carbonyl (═C═O) compound is obtained when the ozonide containing the reducing agent is heated briefly to about 30° C.

13 Claims, No Drawings

METHOD OF MAKING ORGANOSILICON CARBONYL COMPOUNDS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

This invention is directed to organosilicon aldehydes and ketones, methods for their preparation, and more particularly to multi-functional carbonyl functional silanes.

There have been previous attempts to prepare silanes having multi-functional moieties attached to the silicon atom. For example, silanes having non-labile (stable) groups such as alkyl and aryl, together with labile (unstable) aldehyde and ketone groups, are known in the art, as evidenced by U.S. Pat. No. 3,344,104 (Sep. 26, 1967).

However, there is continuing interest in manufacturing other types of multi-functional silanes having several different labile groups attached to the same silicon atom. Such multi-functional silanes can be used in various reactions corresponding to the labile functional groups.

Previous attempts to prepare silanes having another labile group on the same silicon atom have not been successful, however. For example, an attempted addition of methyldiethoxysilane or methyldichlorosilane to acrolein $CH_2=CH-CH=O$ gave only an intractable mixture, *Journal of the American Chemical Society*, Volume 79, Pages 3073–3077, Jun. 25, 1957. Therefore, ozonolysis of silanes containing unsaturation has been developed by the present inventors as a viable alternative procedure.

In this regard, the reaction of ozone ($O_3$) with a carbon-carbon double bond is known. Historically, however, the reaction has only been used as an analytical method to determine the position of a double bond along a hydrocarbon chain. Based on early studies and published reports, it is generally agreed among artisans that an ozonide intermediate is formed upon exposure of the double bond to ozone.

Thus, ozonolysis of alkenes leads to formation of an ozonide intermediate. The ozonide intermediate is a five-member peroxy-ether ring shown below:

in which R1, R2, R3, and R4, are hydrogen, an alkyl group such as methyl, or an aryl group such as phenyl. When R1, R2, R3, and R4, are each hydrogen, for example, the ozonide is 1,2,4-trioxolane. When $R_1$ and R3 are hydrogen, and R2 and R4 are methyl, for example, the ozonide is 3,5-dimethyl-1,2,4-trioxolane.

These ozonide intermediates are not stable, however, and readily rearrange to various hydroperoxides, dimeric and polymeric peroxides, and other oxygen containing compounds. According to the literature, it is generally agreed among artisans that in most cases, these ozonides break down rapidly, and initially form more stable zwitterion intermediates.

But under suitable conditions, a clean and efficient reaction can be attained, and an ozonide can be converted to an organic aldehyde using an appropriate reducing agent and reaction temperature. The solvent plays an important role in the stabilization of ozonide intermediates and their reduction to organic aldehydes. The choice of solvent depends upon the particular alkene being used, and some solvents are more efficient than others.

Thus, some preferred solvents are aprotic solvents such as carbon tetrachloride, methylene chloride $CH_2Cl_2$, and chloroform $CHCl_3$, which lead to high yields of ozonides, which can then be reduced subsequently to organic aldehydes or ketones.

Typical of reducing agents that have been employed in such organic syntheses include sodium iodide in the presence of water, potassium iodide in the presence of water, sodium iodide in the presence of acetic acid, potassium iodide in the presence of acetic acid, zinc in the presence of water, magnesium in the presence of water, zinc in the presence of acetic acid, and magnesium in the presence of acetic acid.

Examples of other reducing agents that can be used in preparing organic aldehydes or ketones from ozonide intermediates are sodium bisulfite $NaHSO_3$, ferrous sulfate $FeSO_4$, potassium ferrocyanide $K_4[Fe(CN)_6]$, stannous chloride $SnCl_2$ in the presence of hydrochloric acid, tin in the presence of hydrochloric acid, ferrous ammonium sulfate $(NH_4)_2Fe(SO_4)_2$, silver nitrate $AgNO_3$, trimethyl phosphite $(CH_3O)_3P$, quinol (hydroquinone) $C_6H_4(OH)_2$, pyridine $N(CH)_4CH$, piperidine $C_5H_{11}N$, sulfur dioxide, and dimethyl sulfide $(CH_3)_2S$.

Despite the fact that such information is available to artisans on converting organic compounds containing unsaturated carbon-carbon double bonds to organic carbonyl compounds by ozonolysis and reduction, the ozonolysis and reduction procedure has not been applied in the conversion of silanes having carbon-carbon double bonds to silicon-containing carbonyl compounds.

In fact, only relatively few procedures have been successful in preparing multi-functional silanes, including for example, the UV irradiation of vinylsilanes in the presence of an organic aldehyde yielding a silicon-containing ketone, *Bulletin of the Academy of Sciences*, USSR Division of Chemical Science, Number 8, Pages 1405–1407, (August 1966); and the reaction of silicon-containing nitriles with a methyl Grignard reagent yielding a silicon-containing ketone, in the *Journal of General Chemistry of the USSR*, Volume 38, Number 2, Pages 380–385, February 1968.

Yet such procedures have not been useful commercially, either because of poor yield, the occurrence of extensive side reactions, or significant costs associated with starting materials or the process itself. Our invention resolves these problems, and provides an efficient method of obtaining multi-functional silanes containing the carbonyl group.

BRIEF SUMMARY OF THE INVENTION

Our invention relates to a method of making an organosilicon carbonyl compound. First, an organosilicon compound containing ozonide functionality is formed by exposing to ozone, an organosilicon compound such as:

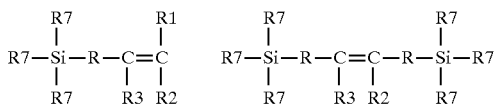

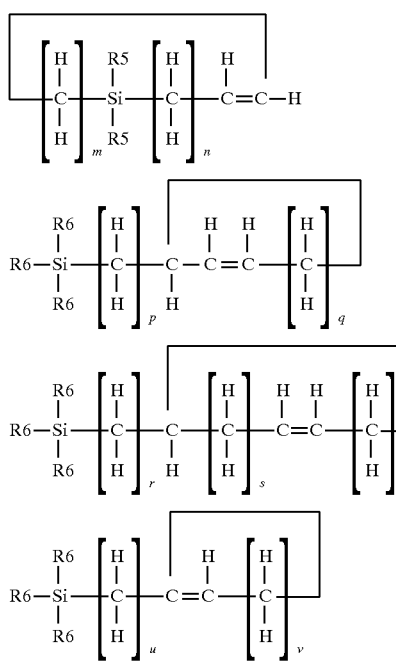

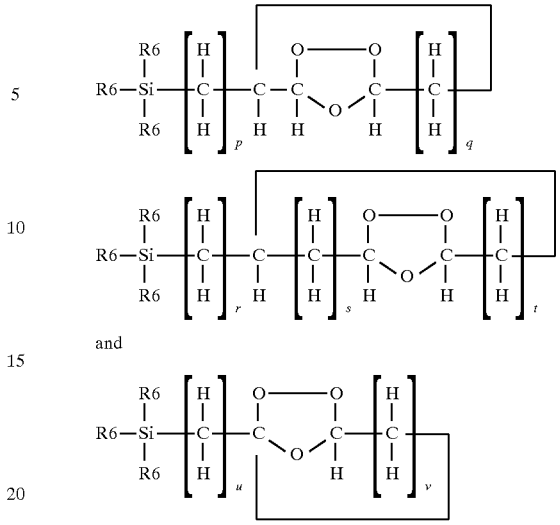

and where R, R1, R2, R3, R5, R6, R7, m, n, p, q, r, s, t, u, and v are the same as defined above.

Our invention also relates to organosilicon aldehydes or ketones prepared according to these methods.

These and other features and objects of our invention will become apparent from a consideration of the detailed description.

BRIEF DESCRIPTION OF THE SEVERAL VIEWS OF THE DRAWING

Not applicable.

DETAILED DESCRIPTION OF THE INVENTION

The present invention relates to aldehyde or ketone functional silanes and methods for their preparation. The silanes have the formula $X_{(4-a-b)}SiR_a^v(R^{vi}-R^{vii})_b$ where a and b each represent an integer. In the formula, a has a value from 0 to 3, b has a value from 1 to 3, and the sum of a and b is less than 4. X represents a hydrolyzable group such as halogen, alkoxy, or acetoxy. $R^v$ can be an alkyl group such as methyl, or an aryl group such as phenyl. $R^{vii}$ represents an aldehyde functionality —CHO or a ketone functionality —$CR^{viii}O$ located on hydrocarbon linking radical $R^{vi}$, so that the aldehyde functionality or the ketone functionality are at least two carbon atoms removed from the silicon atom, i.e., $\equiv Si-(CH_2)_k-CHO$ and $\equiv Si-(CH_2)_k-CR^{viii}O$ where k is =2 or >2. $R^{viii}$ is any saturated hydrocarbon radical or aromatic hydrocarbon radical.

These aldehyde and ketone functional silanes can be manufactured in high yields by (i) the ozonolysis of silanes containing alkenyl groups, followed by (ii) treatment of the ozonide bound silane with a reducing agent, such as zinc and acetic acid, for reducing the ozonide complex to an aldehyde or ketone. The process is capable of being carried out relatively rapidly, and it is economical to the extent that use can be made of readily available starting materials such as hexenyl functional, chloro-, or alkoxysilanes.

The resulting aldehyde and ketone functional silanes can be used in most of the reactions typical to carbonyls, and the silanes can also be used as crosslinking agents, surface treatment agents, or as coatings.

Functional silanes having hydrolyzable substituents, in addition to the unsaturation, are most preferred, such as In these formulas, R is a hydrocarbon linking group containing at least two carbon atoms; R1, R2, and R3, are hydrogen, an alkyl radical, or an aryl radical; R5, R6, and R7 represent an alkyl group, an aryl group, halogen, alkoxy, or acetoxy; m and n each have a value of 2–4; p is 1–4; q is 2–6; r is 0–4; s and t are each 1–6; u is 2–4; and v is 3–7. Preferably, at least one R5, R6, and R7 group in each formula is halogen, alkoxy, or acetoxy.

An organosilicon aldehyde or ketone is then made by reducing the organosilicon compound containing ozonide functionality to the corresponding carbonyl compound.

In simplified terms, our invention then relates to a method of making organosilicon aldehydes or ketones by reducing organosilicon compounds containing ozonide functionality such as:

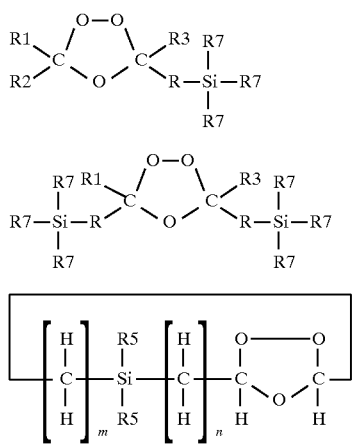

halosilanes, alkoxysilanes, and acetoxysilanes. Some examples of preferred functional silanes are silanes in which the unsaturation is at least two carbon atoms removed from the silicon atom such as 3-butenylmethyldichlorosilane, 5-hexenyldimethylchlorosilane, 5-hexenylmethyldichlorosilane, 5-hexenyltrichlorosilane, 7-octenyldimethylchlorosilane, 7-octenyltrichlorosilane, 1,10-bis(dimethylchlorosilyl)-5-decene, 3-butenyltriethoxysilane, 5-hexenyldimethylmethoxysilane, 5-hexenylmethyldimethoxysilane, and 7-octenyltrimethoxysilane.

While functional silanes having hydrolyzable substituents in addition to unsaturation such as halosilanes, alkoxysilanes, and acetoxysilanes, are most preferred herein, functional silanes having other types of hydrolyzable substituents can be used, such as ketoxime, ureido, carboxyl, sulfate, sulfate ester, cyano, isocyanate, phosphate, and phosphate ester.

Other types of organosilicon compounds containing unsaturation can be used in addition to the functional silanes referred to above. For example, cycloalkenyl silanes can be used, including those types of cycloalkenyl silanes in which the silicon atom constitutes part of a ring structure. Such cycloalkenyl silanes are represented below:

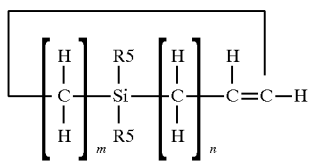

Compounds of this type are described, for example, in the *Journal of Organic Chemistry*, Volume 39 (11), Pages 1539–1542, (1974). In this type of cycloalkenyl silane, m and n each have a value of 2–4, and R5 can be an alkyl radical, an aryl radical, or one of the hydrolyzable groups previously mentioned. As noted above, the unsaturation should be at least two carbon atoms removed from the silicon atom.

In addition, cycloalkenyl silanes can be used of the type in which the silicon atom does not constitute part of a ring structure. Such cycloalkenyl silanes are represented below:

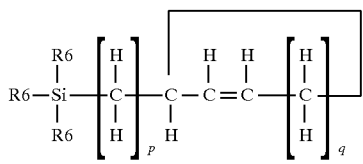

In this type of cycloalkenyl silane, p is 1–4; q is 2–6; and R6 represents an alkyl radical, an aryl radical, or one of the hydrolyzable groups previously mentioned. The unsaturation should be at least two carbon atoms removed from the silicon atom.

An alternate embodiment of the above cycloalkenyl silane is shown below:

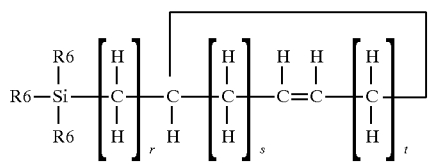

In this embodiment, r is 0–4; s and t are each 1–6; and R6 represents an alkyl radical, an aryl radical, or one of the hydrolyzable groups previously mentioned. The unsaturation should be at least two carbon atoms removed from the silicon atom.

Another type of cycloalkenyl silane which can be used of the type in which the silicon atom does not constitute part of a ring structure is represented below:

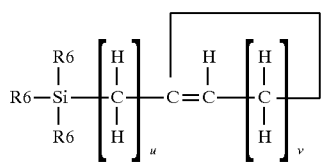

In this cycloalkenyl silane, u is 2–4; v is 3–7; and R6 represents an alkyl radical, an aryl radical, or one of the hydrolyzable groups previously mentioned. The unsaturation should be at least two carbon atoms removed from the silicon atom.

Some examples of functional cycloalkenyl silanes of the type in which the silicon atom does not constitute part of a ring structure are [2-(3-cyclohexenyl)ethyl] dimethylchlorosilane, [2-(3-cyclohexenyl)ethyl] methyldichlorosilane, 3-cyclohexenyltrichlorosilane, [2-(3-cyclohexenyl)ethyl]triethoxysilane, and [2-(3-cyclohexenyl)ethyl]trimethoxysilane.

Our invention can be illustrated schematically in the reaction sequences shown below. For example, the first step in the process utilizes the fact that ozone attaches itself at a double bond to form an ozonide as follows:

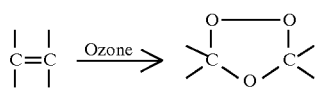

If the double bond is within an organosilane compound, an ozonide bound silane is obtained as follows:

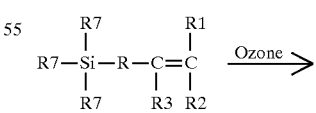

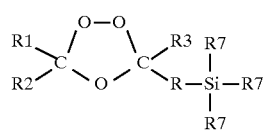

When this ozonide bound silane is reduced, a carbonyl functional silane is obtained as follows:

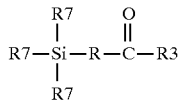

When R3 is hydrogen, an aldehyde functional silane is obtained. When R3 is an alkyl group or an aryl group, a ketone functional silane is obtained.

If the double bond is within an organosilane of the type:

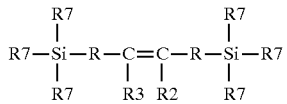

then an ozonide bound silane is obtained of the type:

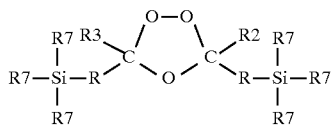

When this ozonide bound silane is reduced, carbonyl functional silanes are obtained as follows:

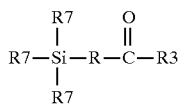

When R3 is hydrogen, two aldehyde functional silanes are obtained. When R3 is an alkyl group or an aryl group, two ketone functional silanes are obtained.

In the following reaction sequence, an ozonide bound cycloalkenyl silane in which the silicon atom is part of a ring structure is obtained as follows:

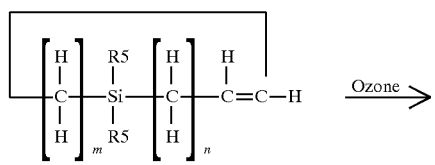

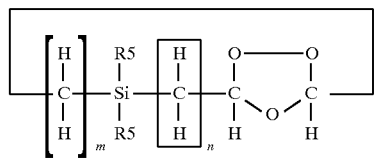

When this ozonide bound cycloalkenyl silane is reduced, an aldehyde functional silane is obtained as follows:

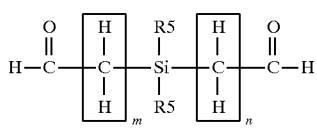

In the following reaction sequence, an ozonide bound cycloalkenyl silane in which the silicon atom is not part of a ring structure is obtained as follows:

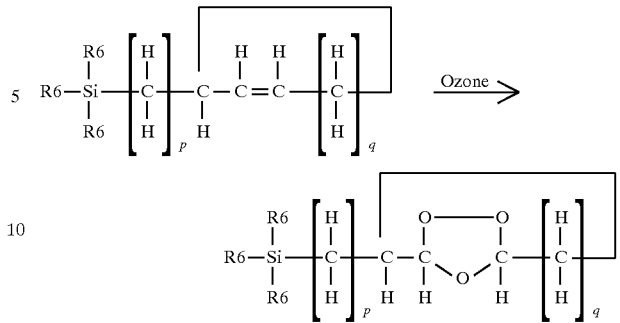

When this ozonide bound cycloalkenyl silane is reduced, an aldehyde functional silane is obtained as follows:

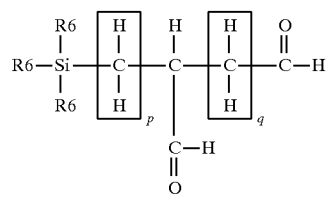

In the following reaction sequence, an alternate embodiment of ozonide bound cycloalkenyl silane in which the silicon atom is not part of a ring structure is obtained as follows:

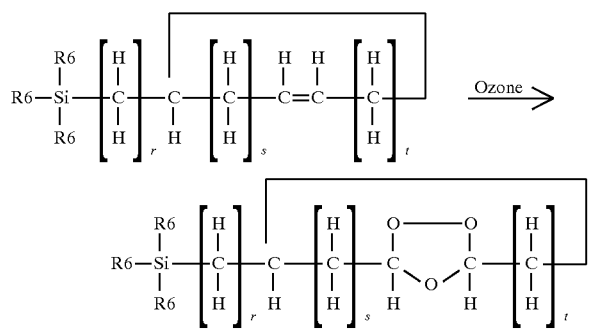

When this ozonide bound cycloalkenyl silane is reduced, an aldehyde functional silane is obtained as follows:

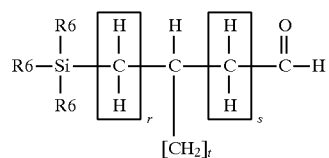

In the following reaction sequence, yet another type of ozonide bound cycloalkenyl silane in which the silicon atom is not part of a ring structure can be obtained as follows:

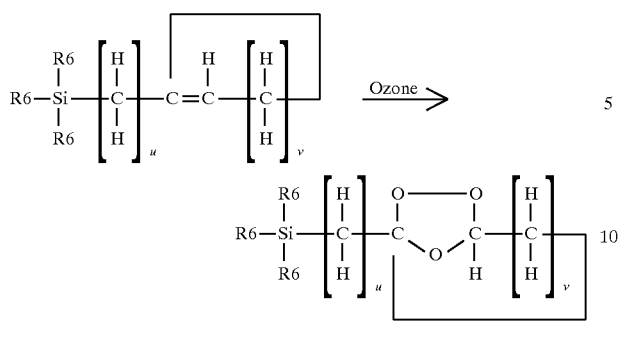

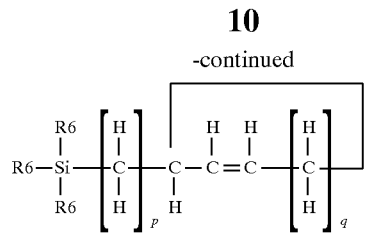

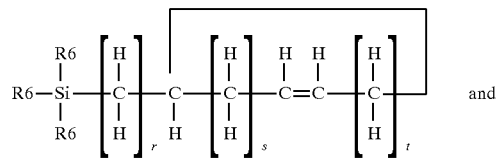

When this ozonide bound cycloalkenyl silane is reduced, an aldehyde and ketone functional silane is obtained as follows:

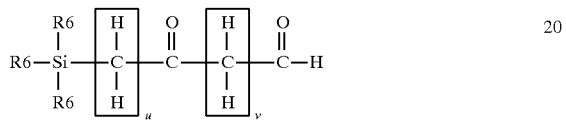

In these formulas, R represents a hydrocarbon linking group and is the residue of the unsaturation. For example, if the unsaturation is 5-hexenyl ($H_2C=CH(CH_2)_4-$) then R is $-(CH_2)_4-$. Preferably, R contains at least two carbon atoms. R1, R2, and R3, are hydrogen, an alkyl radical, or an aryl radical. R5, R6, and R7 represent an alkyl group, an aryl group, halogen, alkoxy, or acetoxy. m and n each have a value of 2–4; p is 1–4; q is 2–6; r is 0–4; s and t are each 1–6; u is 2–4; and v is 3–7.

Following conversion of the silane containing an alkenyl group (Alkene) to an ozonide bound silane (Ozonide), the ozonide bound silane is reduced to an aldehyde functional silane (Aldehyde) as depicted below. In this reaction scheme, the reducing agent is zinc and acetic acid.

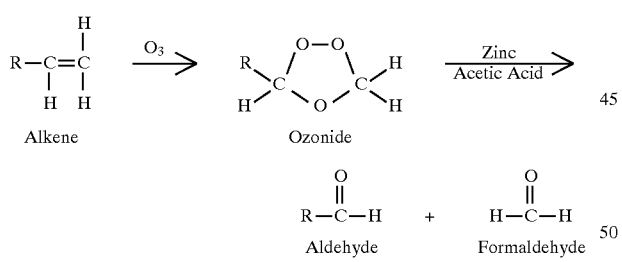

For example, the following silanes containing an alkenyl group can be used to make aldehyde functional silanes:

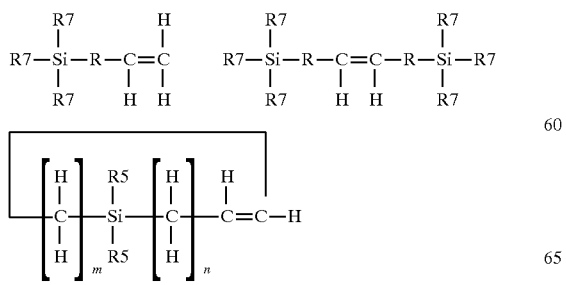

Ketone functional silanes are obtained in the same way as depicted below:

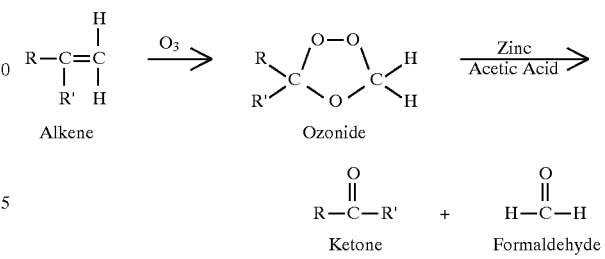

For example, the following silanes containing an alkenyl group can be used to make ketone functional silanes:

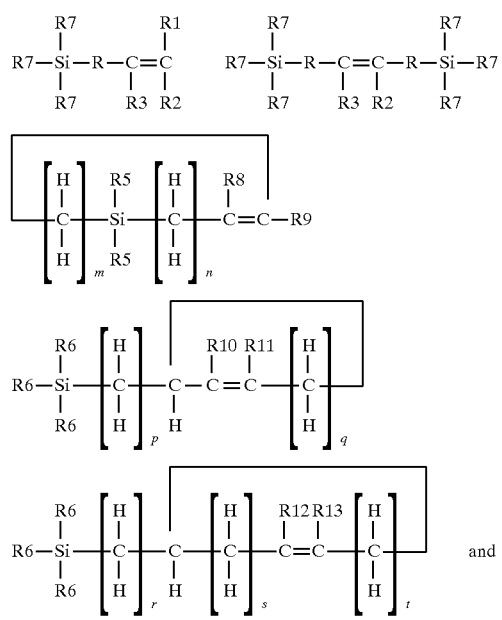

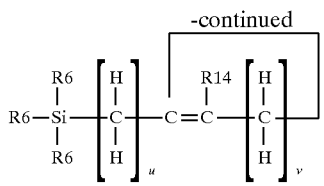

In these formulas, R1 to R3 and R8 to R14 represent alkyl or aryl groups, rather than hydrogen.

Under proper conditions of temperature, reducing agent, and solvent, carbonyl functional silanes can be obtained in high yield. The temperature used to carry out the reaction is not critical, but it should be low enough to increase the solubility of ozone, and prevent the premature decomposition of the ozonide intermediate.

Although it is preferred to carry out the reaction at low temperatures as shown in our Examples 1 and 2, for instance, under certain conditions the lower temperature limit is determined by the freezing point of the solvent. Thus, the reaction temperature must be maintained at least above the freezing point of the solvent.

The invention is illustrated in more detail in the following examples. In these examples, readily available commercial materials were used, i.e., 5-hexenyldimethylchlorosilane $H_2C=CH(CH_2)_4Si(CH_3)_2Cl$ and 5-hexenylmethyldimethoxysilane $H_2C=CH(CH_2)_4Si(OCH_3)_2CH_3$. These functional silanes were converted efficiently and economically to the corresponding carbonyl compound by simply subjecting the silane to ozone for brief periods of time, and then reducing the ozonide bound silane to the corresponding carbonyl functional silane.

EXAMPLE 1

5-hexenyldimethylchlorosilane was dissolved in methylene chloride (17.43 grams in 150 ml) in a three-neck flask equipped with a stirrer. The solution was cooled to −78° C. Ozone was introduced into the bottom of the solution, and was allowed to bubble through the solution at a rate of 0.0213 lb/per hour ($0.0268 \times 10^{-4}$ kilogram per second). After completion of the reaction, the solution was heated briefly to about 30° C. Then equi-molar amounts of zinc and acetic acid (0.124 and 0.120 moles, respectively) were introduced into the solution to reduce the ozonide intermediate to the corresponding aldehyde. Gas Chromatography (GC) and $^{13}$C Nuclear Magnetic Resonance (NMR) indicated complete conversion of the starting material to the aldehyde (5-pentanal)-dimethylchlorosilane.

EXAMPLE 2

Example 1 was repeated under identical conditions using 5-hexenylmethyldimethoxysilane dissolved in methylene chloride (18.61 grams in 150 ml). The ozonolysis reaction was completed after 40 minutes as indicated from an intense blue color. The ozonide intermediate was converted to the corresponding aldehyde in the same fashion as noted in the previous example. GC traces showed that all of the hexenyl functional silane starting material had been consumed (retention time 5.60 minutes), and that a new peak corresponding to the desired aldehyde functional silane was present (retention time 6.40 minutes). Also, $^{13}$C NMR of the starting material and the product showed that no residual double bond remained, and that a new peak (about 203 ppm) corresponding to the aldehyde (5-pentanal)-methyldimethoxysilane was present.

EXAMPLE 3

Comparison

For comparison, an ozonolysis reaction was conducted using 1-hexene $CH_3CH_2CH_2CH_2CH=CH_2$ (8.5 grams) in methylene chloride (150 ml) at −78° C. for 30 minutes. A very unstable ozonide was obtained. It rapidly decomposed in an uncontrolled exothermic reaction, and splashed out of the reaction flask shortly after it had been treated with zinc and acetic acid.

The presence of the silane in our Examples 1 and 2 by comparison, moderates the rate of the decomposition reaction, and reduces the risk of explosion, although extreme caution is still recommended when dealing with highly oxygenated and unstable ozonide intermediates.

An advantage of our method is its simplicity, and its use of readily available starting materials. In addition, the reaction is relatively fast, and leads to high yields with little or no complications associated with by-products. Our method also allows one to prepare multi-functional silanes containing substituents such as halogen, alkoxy, and acetoxy which are not destroyed during ozonolysis, nor do such substituents interfere with the process.

Other variations may be made in compounds, compositions, and methods described herein without departing from the essential features of our invention. The forms of our invention are exemplary only and are not intended as limitations on its scope as defined in the appended claims.

We claim:

1. A method of making an organosilicon carbonyl compound comprising forming an organosilicon compound containing ozonide functionality by exposing to ozone an organosilicon compound selected from the group consisting of

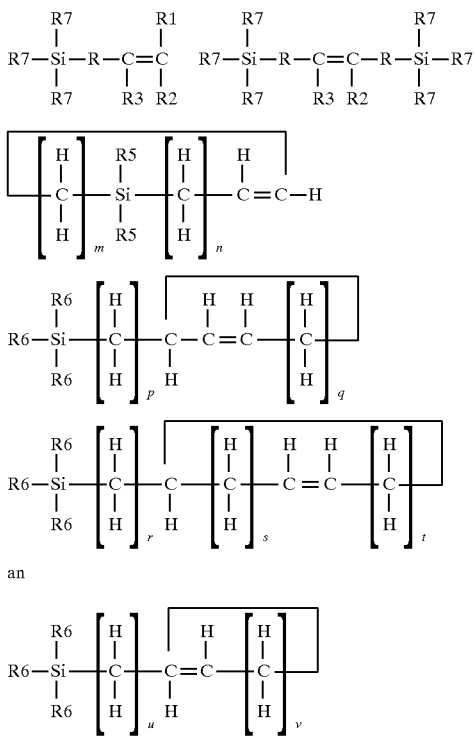

in which R is a hydrocarbon linking group containing at least two carbon atoms; R1, R2, and R3, are hydrogen, an alkyl radical, or an aryl radical; R5 and R7 represent an alkyl group, an aryl group, halogen, alkoxy, or acetoxy; R6 represents an aryl group, halogen, or acetoxy; m and n each have a value of 2–4; p is 1–4; q is 2–6; r is 0–4; s and t are each 1–6; u is 2–4; v is 3–7; and reducing the organosilicon compound containing ozonide functionality to an organosilicon carbonyl compound.

2. A method according to claim 1 in which the organosilicon compound containing ozonide functionality is reduced to an organosilicon carbonyl compound with a reducing agent selected from the group consisting of sodium iodide, potassium iodide, zinc, magnesium, sodium bisulfite, ferrous sulfate, potassium ferrocyanide, stannous chloride, tin, ferrous ammonium sulfate, silver nitrate, trimethyl phosphite, quinol, pyridine, piperidine, sulfur dioxide, and dimethyl sulfide.

3. A method according to claim 2 in which the organosilicon compound containing ozonide functionality is reduced to an organosilicon carbonyl compound with a reducing agent in the presence of a solvent selected from the group consisting of carbon tetrachloride, methylene chloride, and chloroform.

4. A method according to claim 3 in which the method is carried out at a temperature above the freezing point of the solvent.

5. A method of making an organosilicon carbonyl compound comprising reducing an organosilicon compound containing ozonide functionality selected from the group consisting of

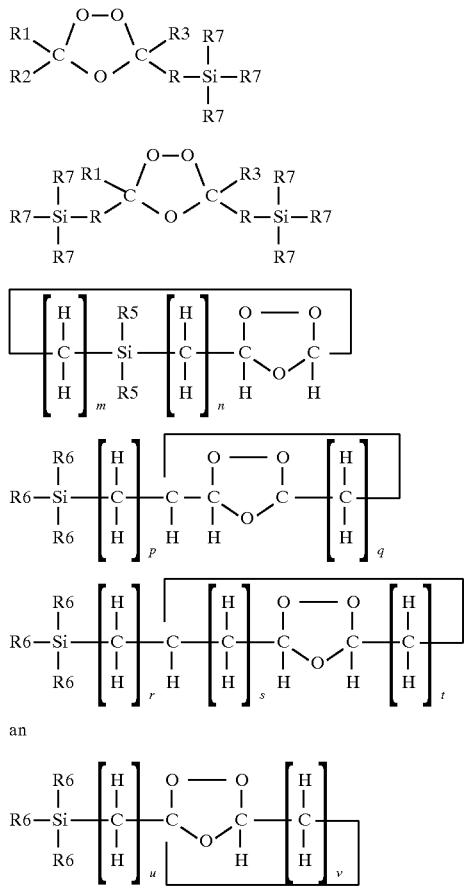

in which R is a hydrocarbon linking group containing at least two carbon atoms; R1, R2, and R3, are hydrogen, an alkyl radical, or an aryl radical; R5 and R7 represent an alkyl group, an aryl group, halogen, alkoxy, or acetoxy; R6 represents an aryl group, halogen, or acetoxy; m and n each have a value of 2–4; p is 1–4; q is 2–6; r is 0–4; s and t are each 1–6; u is 2–4; and v is 3–7.

6. A method according to claim 5 in which the organosilicon compound containing ozonide functionality is reduced to an organosilicon carbonyl compound with a reducing agent selected from the group consisting of sodium iodide, potassium iodide, zinc, magnesium, sodium bisulfite, ferrous sulfate, potassium ferrocyanide, stannous chloride, tin, ferrous ammonium sulfate, silver nitrate, trimethyl phosphite, quinol, pyridine, piperidine, sulfur dioxide, and dimethyl sulfide.

7. A method according to claim 6 in which the organosilicon compound containing ozonide functionality is reduced to an organosilicon carbonyl compound with a reducing agent in the presence of a solvent selected from the group consisting of carbon tetrachloride, methylene chloride, and chloroform.

8. A method according to claim 7 in which the method is carried out at a temperature above the freezing point of the solvent.

9. An organosilicon carbonyl compound selected from the group consisting of

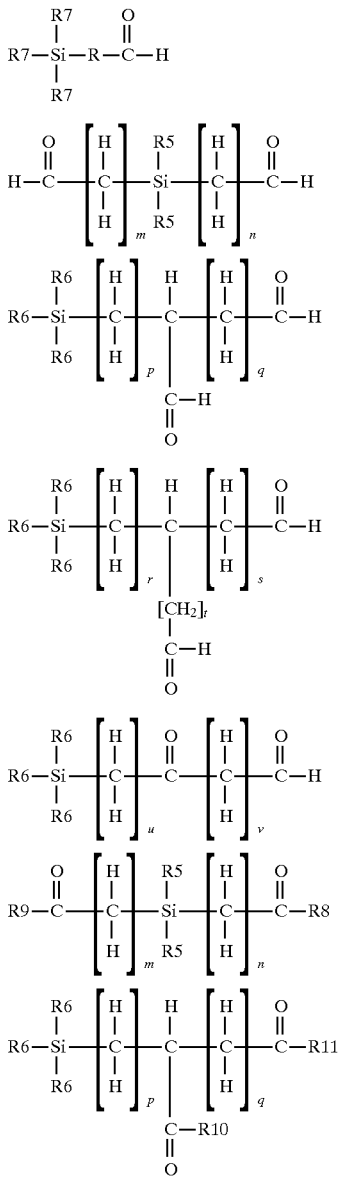

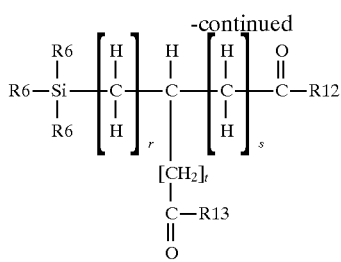

and

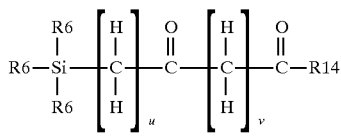

where R represents a hydrocarbon linking group containing at least two carbon atoms; R5 in each formula is an alkyl group, an aryl group, halogen, alkoxy, or acetoxy, provided at least one R5 group in each formula is halogen, alkoxy, or acetoxy; R6 in each formula is an aryl group, halogen, or acetoxy; R7 represents an aryl group or acetoxy; R8–R14 represent an alkyl radical or an aryl radical; m and n each have a value of 2–4; p is 1–4; q is 2–6; r is 0–4; s and t each have a value of 1–6; u is 2–4; and v is 3–7.

10. Compounds of the formula

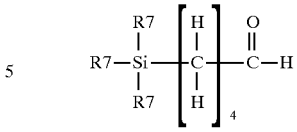

where R7 represents an alkyl group, an aryl group, halogen, or acetoxy, provided at least one R7 group is halogen or acetoxy.

11. Compounds according to claim 10 in which each R7 group represents a chloro group.

12. Compounds according to claim 10 in which one R7 group represents a chloro group and the two remaining R7 groups represent methyl groups.

13. A method of making an organosilicon carbonyl compound comprising forming an organosilicon compound containing ozonide functionality by exposing to ozone an organosilicon compound selected from the group consisting of 5-hexenyldimethylchlorosilane and 5-hexenylmethyldimethoxysilane; and reducing the organosilicon compound containing ozonide functionality to an organosilicon carbonyl compound.

* * * * *